United States Patent [19]

Quest

[11] Patent Number: 4,520,803
[45] Date of Patent: Jun. 4, 1985

[54] ORTHOPAEDIC APPARATUS

[76] Inventor: Thomas A. Quest, 9205 Timberline Dr., Omaha, Nebr. 68152

[21] Appl. No.: 581,889

[22] Filed: Feb. 21, 1984

[51] Int. Cl.³ .............................................. A61F 3/00
[52] U.S. Cl. .................................................. 128/80 A
[58] Field of Search ................. 128/80 R, 80 A, 80 F, 128/88

[56] References Cited

U.S. PATENT DOCUMENTS

| | | | |
|---|---|---|---|
| 2,963,020 | 12/1960 | Moran | 128/80 A |
| 3,109,424 | 11/1963 | Brachman | 128/80 A |
| 4,088,129 | 5/1978 | DiGiucio | 128/80 A |
| 4,249,523 | 2/1981 | Bidwell | 128/80 A |

Primary Examiner—John D. Yasko
Attorney, Agent, or Firm—George R. Nimmer

[57] ABSTRACT

Disclosed is orthopaedic apparatus for comfortably maintaining a selectable eversion-angle between the sole-axes of a reclining patient's shoes. As in the prior art, each of the patient's two shoes is equipped with a shoe-stud, there being a plate member angularly rotatable about the shoe-stud and carrying a radially-offset and laterally extending primary-pivot station; the two primary-pivots are longitudinally bridged with a laterally rigid splint. Departing from the prior art, the novel orthopaedic splint of the present invention includes at least two splint-pivots within the longitudinal splint-length which do not detract from the required lateral rigidity, but which splint-pivots do permit splint movement in a plane intersecting the primary-pivots and thereby offer more comfort to and growth accommodation for a patient being orthopaedically treated for internal tibial distortion.

7 Claims, 7 Drawing Figures

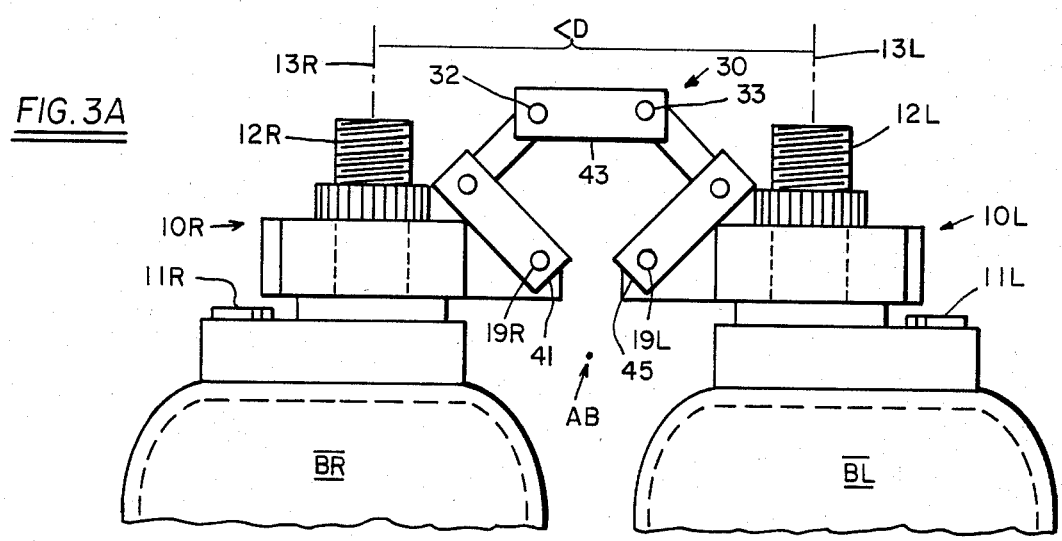
FIG. 3A
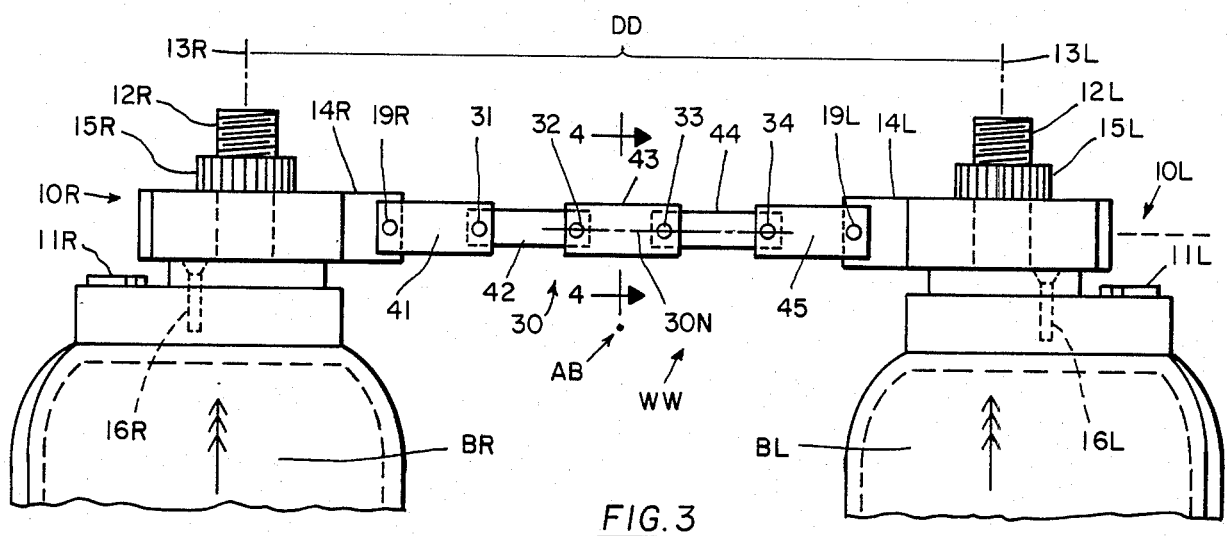
FIG. 3
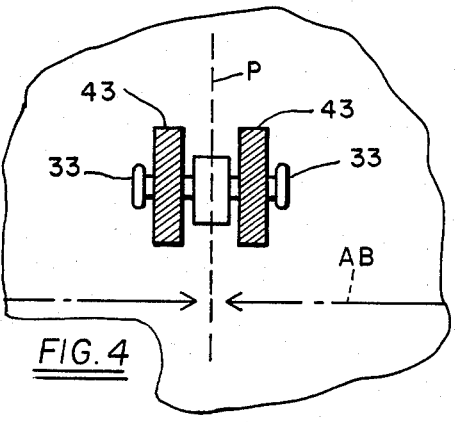
FIG. 4
FIG. 5
| MAKE SPLINT-LENGTH EXCEED PELVIC-WIDTH | SPACE STUD-AXES WITH SPLINT-LENGTH |

ORTHOPAEDIC APPARATUS

BACKGROUND OF THE INVENTION

In the orthopaedics healing arts, skeletal deformities of the lower legs can be treated with orthopaedically encumbered footwear during noctural sleeping hours. With such orthopaedic treatment being utilized during the night time, the patient is wholly encumbered by any orthopaedic apparatus during daytime hours i.e. during day time, the patient can wear normal walking shoes completely unencumbered by non-ambulatory orthopaedic apparatus. However, at bed time, the patient continues wearing the day time footwear, but with a nocturnal installation of an orthopaedic apparatus encumberance which tends to correct the skeletal deformation. For example, if the patient is suffering from internal tibial distortion, the orthopaedic appliance sets the patient's footwear to an orthopaedically prescribed eversion-angle.

The aforementioned prior art is typically illustrated in drawing FIGS. 1 and 1A and wherein "BL" and "BR" refer to the shoebottoms of a patient's left and right shoes positioned supinely upon longitudinal sleeping bed "H" and wherein "AL" and "AR" refer to the respective sole-axes. "W" indicates a typical prior art apparatus employed to maintain the upright sole-axes "AL" and "AR" at an orthopaedically prescribed selectable eversion-angle bisected by laterally extending line "AB". Apparatus "W" comprises three main components including substantially identical shoe-connectors 10L and 10R terminating at laterally extending primary-pivots 19L and 19R, and a laterally rigid splint means 20 extending lengthwise longitudinally along horizontal axis 20H and pivotably connected at primary-pivots 19L and 19R.

It is the purpose of prior art shoe-connectors e.g. 10L and 10R, to provide a selectable and maintainable angle e.g. TL° and TR°, between the laterally extending primary-pivots (19L and 19R) and the respective stud-axes 13L and 13R of shoe-studs 12L and 12R. In this regard, the shoe-connectors are so attached to the shoes that the stud-axes (13L and 13R) intersect the two shoes at similar locations whereby axes 13L and 13R are parallel. For example, with shoe-connectors 10L and 10R, the shoe-studs are attached with fasteners (e.g. 16R) to the shoe heels bottoms. Plate members (e.g. 14L, 14R) are angularly rotatable about the shoe-studs and carry the primary-pivots (e.g. 19L, 19R) outwardly from stud-axes 13L and 13R, the selectable angles TL° and TR° being indicatable at angular indicia 11L and 11R. The selected angles (e.g. TL°, TR°) are thereafter maintainable, as by nuts 15L and 15R threadedly engaged with the shoe-studs and bearing downwardly against the appropriately angularly rotated plate members 14L and 14R.

It is the purpose of the prior art splint means to maintain the angles TL° and TR° which determine the eversion-angle bisected by lateral line "AB". Accordingly, a longitudinal splint bridge needs to be laterally rigid throughout a "splint-length", defined as its longitudinal length between its pivotal-connections (e.g. 19L, 19R) to the shoe-connectors (e.g. 10L, 10R). In this regard, prior art splint bridges, such as shown at 20, typically comprise a structurally monolithic metallic bar which is rigid along all planes thereof. Though the patient's legs are able to flex such apparatus "W" at primary-pivots 19L and 19R, and thereby adductionally attain some limited relief of apparatus tedium without disturbing the eversion-angle, the pedal adductional movement is so limited that the patient's sleep becomes fitfull and frequently interrupted by muscular tension. Also in the prior art, the monolithic splint-length needs to be empirically chosen so that the apparatus longitudinal "D" length 13L-13R along axis 20H does not exceed the pelvic width lest ligamentous problems accompany patient usage of typical apparatus "W". However, with structurally monolithic and pelvic-width prior art splints, the patient is precluded from relieving apparatus tedium by abductional feet movement, thereby providing also abductional restraint interference to restful sleep. Moreover, the such prior art apparatus needs to be periodically structurally modified to accommodate growing children, such as by periodically substituting progressively longer monolithic splint-lengths according to the patient's skeletal growth process. These periodic structural modifications to typical prior art apparatus "W" can be exceedingly expensive, depending upon the child's rate of body growth.

OBJECT OF THE INVENTION

It is accordingly the general objective of the present invention to provide orthopaedic apparatus for treating skeletal deformations (such as internal tibial torsion) and which overcomes disadvantages and deficiencies plagueing the prior art. Among the general objectives are the provision of orthopaedic apparatus for treating internal tibial torsion that: offers more comfort to the patient without detracting from the required therapeutic eversion-angle, including such markedly improved adductional feet movement that the patient can substantially achieve even side-by-side adduction, and the provision of abductional feet movement; and minimizes the frequency of splint-length restructuring as the skeletal growth of a child patient progresses during its long-term orthopaedic treatment program.

GENERAL STATEMENT OF THE INVENTION

With the above general objective in view, and other more specific objectives which will become apparent as this description proceeds, the novel orthopaedic apparatus of the present invention departs from the prior art and instead utilizes, as the longitudinally extending splint bridge, a splint-length interrupted by at least two laterally extending splint-pivots and with at least three intervening splint-links having a single direction of free movement restricted to a single plane. In the case of internal tibial torsion treatment, the single plane substantially perpendicularly intersects the two primary-pivots at the prior art shoe-connectors and the two or more splint-pivots.

GENERAL DESCRIPTION OF THE DRAWING

In the drawing, wherein like characters refer to like parts in the several views, and in which:

FIG. 1, aforedescribed, is a plan view of a prior art orthopaedic apparatus applied to the footwear shoes of a supine patient being treated for internal tibial torsion;

FIG. 1A, aforedescribed, is a sectional elevational view taken along lines 1A'1A of FIGS. 1 and 2;

FIG. 3 is an elevational view taken along line 3—3 of FIG. 2;

FIG. 3A is an elevational view in the direction similar to that of FIG. 3, but showing adductional movement commencing from the FIG. 3 condition;

FIG. 4 is a sectional view taken along line 4—4 of FIG. 3; and

FIG. 5 is a schematic flow diagram referring to clinical implementation of the novel orthopaedic apparatus.

DETAILED DESCRIPTION OF THE DRAWING

Figure 1:
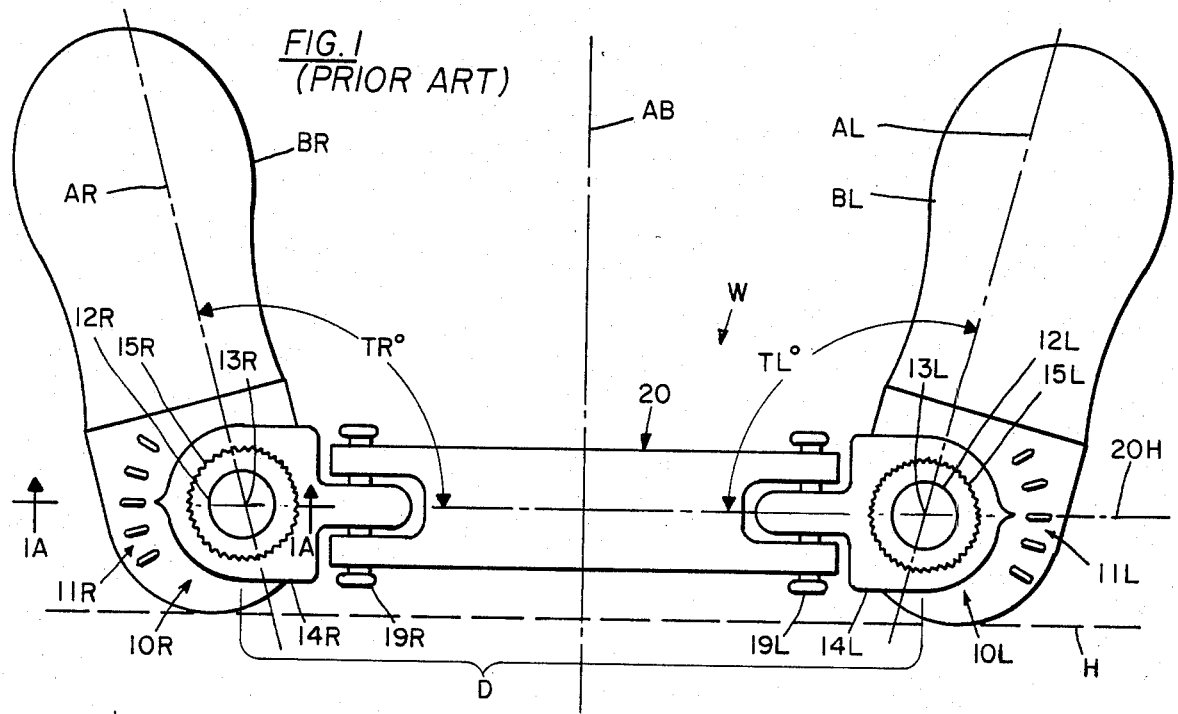
Figure 2:
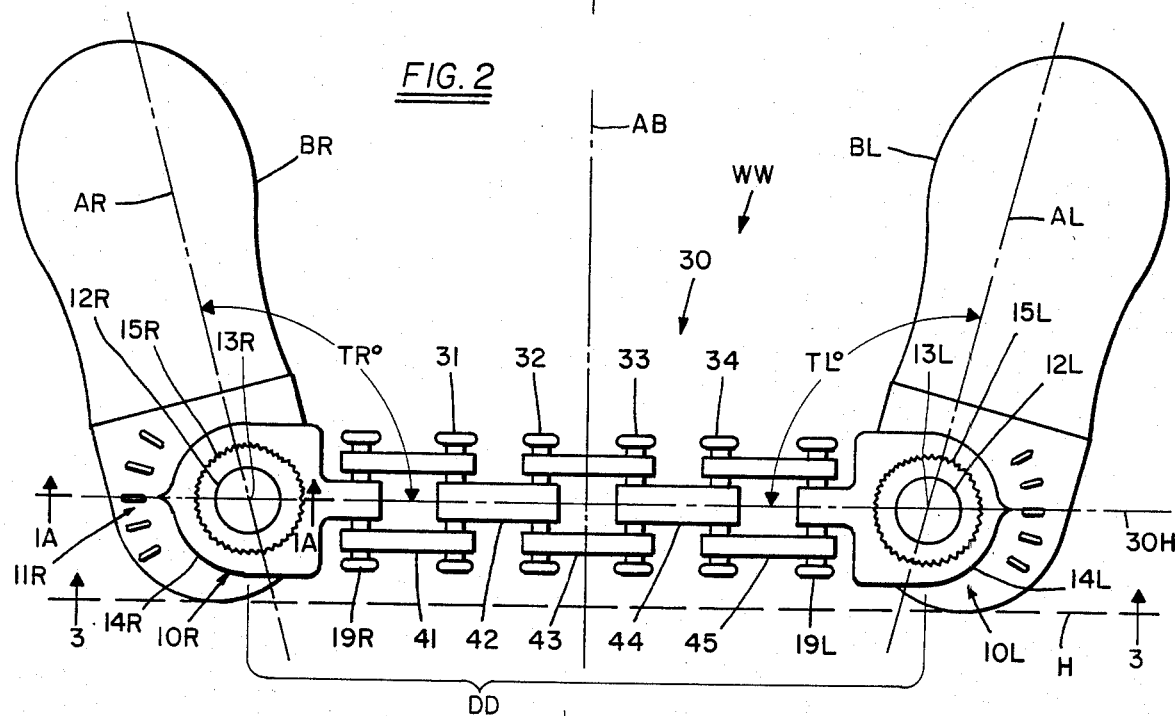
FIG. 2 is a plan view, similar to FIG. 1, of a representative embodiment "WW" of the orthopaedic apparatus of the present invention.
Figure 1A:
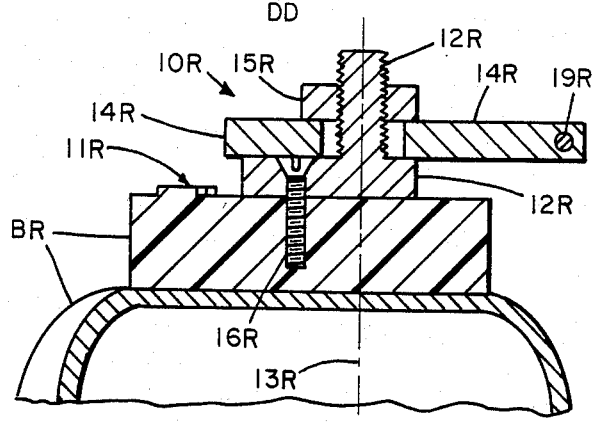

As indicated by sectional elevational FIG. 1A taken from FIGS. 1 and 2, and considering that like characters refer to like parts in the several views, apparatus embodiments "W" and "WW" both utilize like shoe-connectors e.g. 10 having laterally extending primary-pivot 19 offset from the shoe-stud (e.g. 12). Though the orthopaedic apparatus of the present invention (e.g. "WW") adopts usage of prior art primary-pivots (e.g. 19) as the pivotal connections for the longitudinally extending and laterally rigid splint bridge, a comparison of drawing parts 20 and 30 reveals the present invention radically departs from the prior art at the splint bridge. However, as indicated by the confronting arrows of FIG. 4, the splint bridges of the prior art (e.g. 20) and of the invention (e.g. 30) both necessarily possess lateral directional rigidity throughout the longitudinal splint-length (19—19) whereby the prescribed eversion-angle (bisected by line "AB") will be maintained.

Representative embodiment bridging splint 30 of the present invention has its longitudinally extending splint-length 19—19 interrupted by at least two laterally extending parallel splint-pivots (e.g. 32, 34). In this vein, the splint-length 19-19: includes at least three intervening splint-links (e.g. 41, 42-44, 45); is laterally rigid longitudinally throughout, both at the splint-pivots and at the splint-links; and (as seen in FIG. 3A) has a single plane of free movement in a movement plane "P" perpendicularly intersecting the two primary-pivots (19) and the splint-pivots. Such splint-pivots interrupted bridging splints provide exceedingly profound comfort and economic benefits to orthopaedic patients, as demonstrated by physician affidavit testimony appended to this patent application. In summary, these benefits include:

(a) as evident from FIG. 3A, markedly improved capability for adductional movement of the patient's feet, while maintaining the orthopaedically prescribed eversion-angle between the feet;

(b) introduction of an abductional movement capability for the patient's feet, while maintaining the orthopaedically prescribed eversion-angle between the feet; and (c) as indicated by apparatus longitudinal length DD which exceeds the prior art longitudinal length D, a given splint-length automatically accommodates to significant skeletal growth for growing children.

Though provision of the latest two splint-pivot interruptions suffices for the purposes and objectives of the present invention, there is some degree of proportional correlation between the number of splint-pivots and resultant capability for the orthopaedic apparatus. Similarly, it is preferable that the splint-pivots be regularly incrementally spaced along the splint-length 19—19. In these regards, splint embodiment 30 employs four regularly spaced splint-pivots 31–34 whereby there are five substantially equal-length intervening splint-links 41-45 having freedom to pivotably move in but said single plane "P". The required lateral rigidity over the entire splint-length 19—19 is evident in FIG. 4, being schematically indicated by the confronting arrows, and being structurally indicated by the dual-heads splint-pivots (31, 32, 33, etc.).

Operation of representative embodiment "WW", wherein the laterally rigid splint 30 comprises pivotably associated splint-links having movement restricted in the single plane "P", might be summarized as follows. By virtue of such pivotably associated splint-links, it is unnecessary to limit the apparatus longitudinal length 13—13 to a value D not exceeding the patient's pelvic width. In fact, for apparatus "WW", the splint-length 19—19 is selected of sufficient length that apparatus length 13—13 is a value DD substantially exceeding the patient's pelvic width. Such heretofore unusual length DD does not present patient ligamentous problems inasmuch as the splint-links are free to pivotably move in plane "P", and does offer the following ancillary advantages:

(1) introduces an abductional movement capability for the patient's feet, thereby improving patient comfort; and (2) a single splint-length 19—19 automatically accommodates to a long-term orthopaedic treatment program for a growing child, and thereby reduces apparatus maintenance costs.

And another virtue of such pivotably associated splint-links is a profound improvement in adductional movement capability and thereby also improving patient comfort. For example, as indicated in FIG. 3A, the patient may move the feet adductionally and even to the extent of achieving substantial side-by-side contact of the shoe-bottoms. And, as indicated by triple-headed arrows in FIG. 3, the patient may effect relative movement of the feet in directions parallel to the torso length.

As previously alluded to, the Affidavits of medical doctors Walter W. Huurman and L. Joseph Fisher are appended to this patent application following the inventor's formal Declaration and Petition.

From the foregoing, the construction and operation of the orthopaedic apparatus and its method of use will be readily understood and further explanation is believed to be unnecessary. However, since numerous modifications and changes will readily occur to those skilled in the art, it is not desired to limit the invention to the exact construction shown and described, and accordingly, all suitable modifications and equivalents may be resorted to, falling within the scope of the appended claims.

I claim:

1. Orthopaedic apparatus for comfortably maintaining a selectable eversion-angle between the sole-axes of a longitudinally separated pair of shoes, the eversion-angle bisection extending directionally laterally and substantially perpendicular to said longitudinal shoes spacing, said apparatus comprising:

A. a pair of shoe-connectors and each including a shoe-stud extending along a stud-axis, means for attaching the shoe-connectors to the shoes pair in a condition wherein the stud-axes intersect the two shoes at similar locations and are substantially parallel to each other, each shoe-connector including a plate member angulary rotatable about the shoe-stud and the plate member carrying a laterally extending primary-pivot outwardly offset from the shoe-stud, and means for maintaining a selected angular rotation between the plate member at the primary-pivot and the stud-axis; and B. a longitudinally extending splint having two longitudinally separated positions thereof pivotably connected to said two laterally extending primary-pivots whereby a longitudinally extending finite splint-length exists between said two primary-pivots, said splint-length being interrupted by at least two laterally extending splint-pivots and being substantially laterally rigid throughout said splint-length including at the splint-pivots, whereby said splint-length includes at least three intervening splint-links having a single direction of free movement restricted to a movement plane substantially perpendicularly intersecting the two primary-pivots and the splint-pivots.

2. The orthopaedic apparatus of claim 1 wherein the splint-pivots are spaced at substantially equal increments along said splint-length, and the intervening splint-links are of substantially equal lengths.

3. The apparatus of claim 2 wherein there are at least three said regularly spaced splint-pivots.

4. The apparatus of claim 3 wherein there are at least four said regularly spaced splint-pivots and at least five said substantially equal lengths splint-links.

5. The orthopaedic apparatus of claim 1 wherein there are at least three splint-pivots and at least four said intervening splint-links.

6. The orthopaedic apparatus of claim 1 wherein said movement plane also passes along said two stud-axes.

7. Method for orthopaedically treating a child patient suffering from internal tibial torsion, said method comprising the following steps:
   A. measuring the patient's pelvic-width;
   B. connecting to each of the patient's two footwear shoes a shoe-stud extending along a stud-axis and in condition wherein said stud-axes are substantially parallel, and for each shoe-stud selecting and thereafter maintaining a therapeutic angular relationship between a laterally extending primary-pivot and the stud-axis; and
   C. longitudinally bridging said two laterally extending primary-pivots with a longitudinally extending splint, said splint:
      (i) being interrupted therealong by at least two laterally extending splint-pivots,
      (ii) being substantially laterally rigid along the splint length including at the splint-pivots, and
      (iii) having at least three splint-links intervening between said splint-pivots and having free pivotal movements restricted to a movement plane substantially perpendicularly intersecting the primary-pivots and the splint-pivots.

* * * * *